(12) United States Patent
Liao et al.

(10) Patent No.: US 10,195,231 B2
(45) Date of Patent: Feb. 5, 2019

(54) MODIFIED NATURAL KILLER CELLS, COMPOSITIONS AND USES THEREOF

(71) Applicant: Academia Sinica, Taipei (TW)

(72) Inventors: Nan-Shih Liao, Taipei (TW); Jan-Mou Lee, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/109,537

(22) PCT Filed: Dec. 23, 2014

(86) PCT No.: PCT/CA2014/051264
§ 371 (c)(1),
(2) Date: Jul. 1, 2016

(87) PCT Pub. No.: WO2015/100495
PCT Pub. Date: Jul. 9, 2015

(65) Prior Publication Data
US 2016/0324895 A1 Nov. 10, 2016

Related U.S. Application Data

(60) Provisional application No. 61/923,354, filed on Jan. 3, 2014.

(51) Int. Cl.
*A61K 35/17* (2015.01)
*C12N 5/0783* (2010.01)
*A61K 38/20* (2006.01)
*A61K 38/21* (2006.01)

(52) U.S. Cl.
CPC ............. *A61K 35/17* (2013.01); *C12N 5/0646* (2013.01); *C12N 2501/2312* (2013.01); *C12N 2501/2315* (2013.01); *C12N 2501/24* (2013.01)

(58) Field of Classification Search
CPC .................. A61K 35/17; C12N 5/0646; C12N 2501/2312; C12N 2501/2315; C12N 2501/24
USPC ...................................................... 424/93.71
See application file for complete search history.

(56) References Cited

U.S. PATENT DOCUMENTS

| 2014/0010793 A1 | 1/2014 | Lee |
| 2014/0011230 A1 | 1/2014 | Lee |
| 2014/0011276 A1 | 1/2014 | Lee |

FOREIGN PATENT DOCUMENTS

| WO | WO 03/022225 A2 | 3/2003 |
| WO | WO 2007/071388 A1 | 6/2007 |
| WO | WO 2011/053223 A1 | 5/2011 |

OTHER PUBLICATIONS

Choi et al., Interkeukin-15 Enhances Cytotoxicity, Receptor Expression, and Expansion of Neonatal Natural Killer Cells in Long-Term Culture, Clinical and Diagnostic Laboratory Immunology, Sep. 2004, pp. 879-888.*
Chaput, et al., "Phase I clinical trial combining imatinib mesylate and IL-2 HLA-DR+NK cell levels correlate with disease outcome", OncoImmunology 2:2, pp. e23080-1-e23080-10, Feb. 2013.
Evans et al., "A distinct subset of human NK cells expressing HLA-DR expand in response to IL-2 and can aid immune responses to BCG", European Journal of Immunology, vol. 41, No. 7 2011, pp. 1924-1933.
Tsuda et al., "Involvement of CD56brightCD11c+ Cells in IL-18—Mediated Expansion of Human gd T Cells", The Journal of Immunology, vol. 186, No. 4, 2011, 11 pages.
Guimont-Desrochers et al., "Revisiting the prominent anti-tumoral potential of pre-mNK cells", Dec. 11, 2013, vol. 4, Article 446, 9 pages.
Souza et al., "Interleukin-21 expanded NKDC in vitro reduces the B16F10 tumor growth in vivo", Cytokine, 2013, vol. 61, No. 1, pp. 154-160.

* cited by examiner

*Primary Examiner* — Jennifer M. H. Tichy
(74) *Attorney, Agent, or Firm* — Haverstock & Owens LLP

(57) ABSTRACT

Modified natural killer cells, pharmaceutical compositions comprising the modified natural killer cells and at least one pharmaceutically acceptable carrier or excipient, uses of the modified natural killer cells, and methods for identifying depleted natural killer cells and culturing the modified natural killer cells are provided.

6 Claims, 21 Drawing Sheets

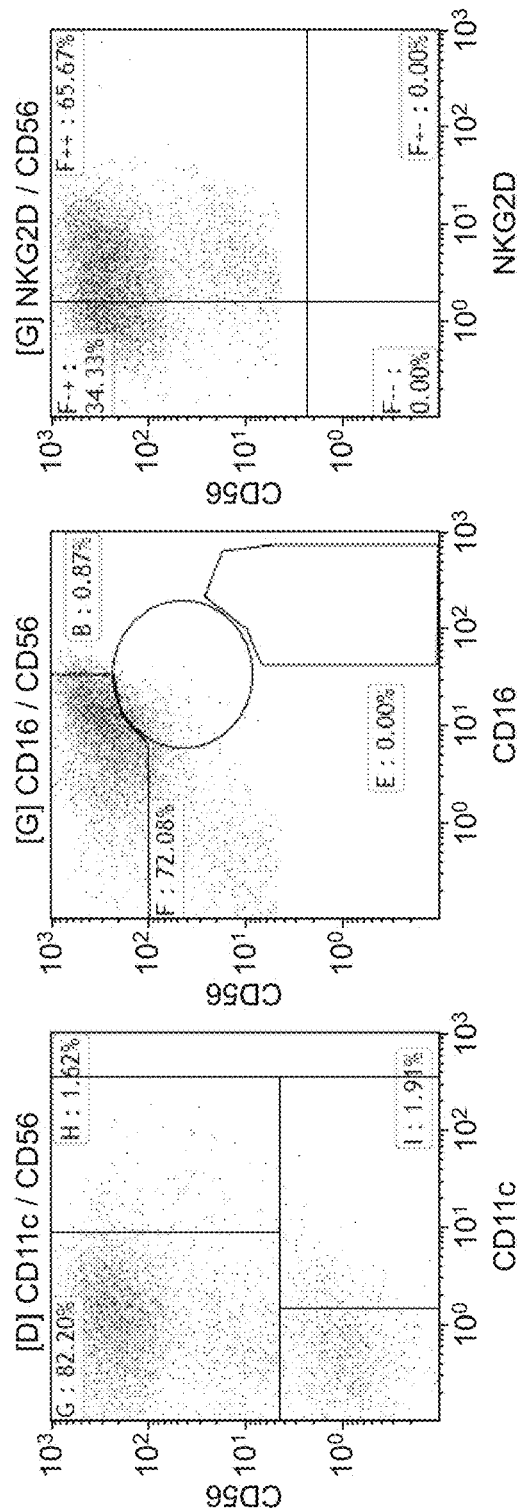

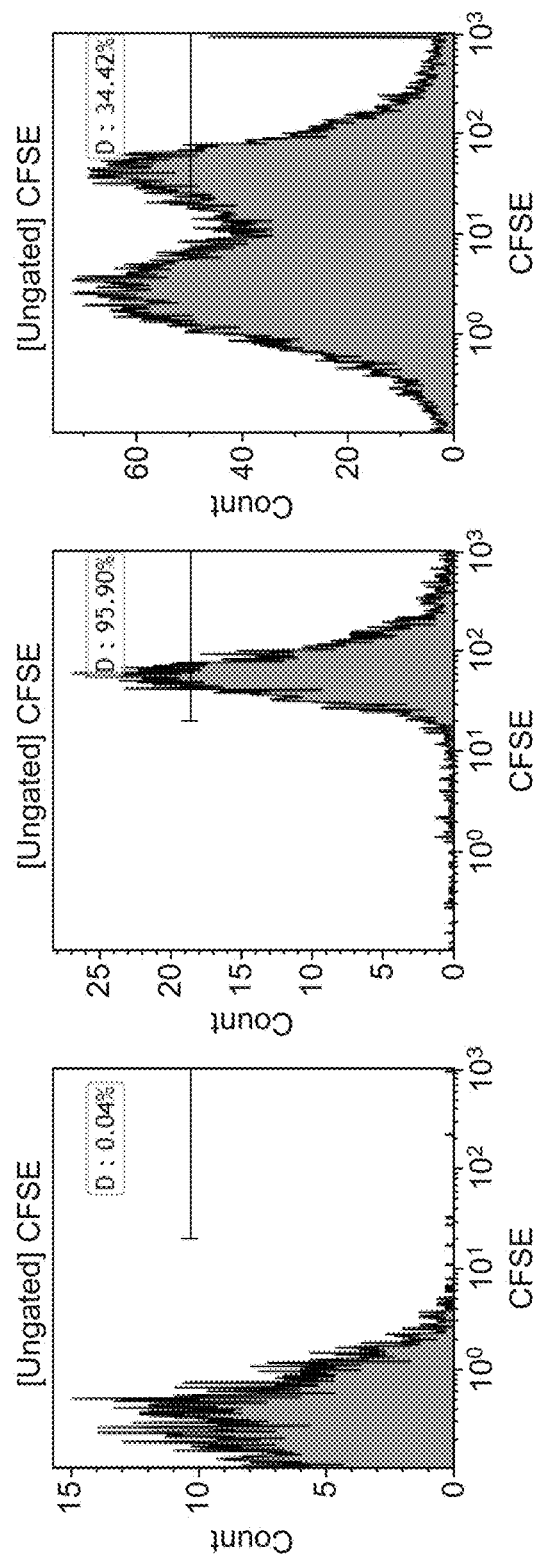

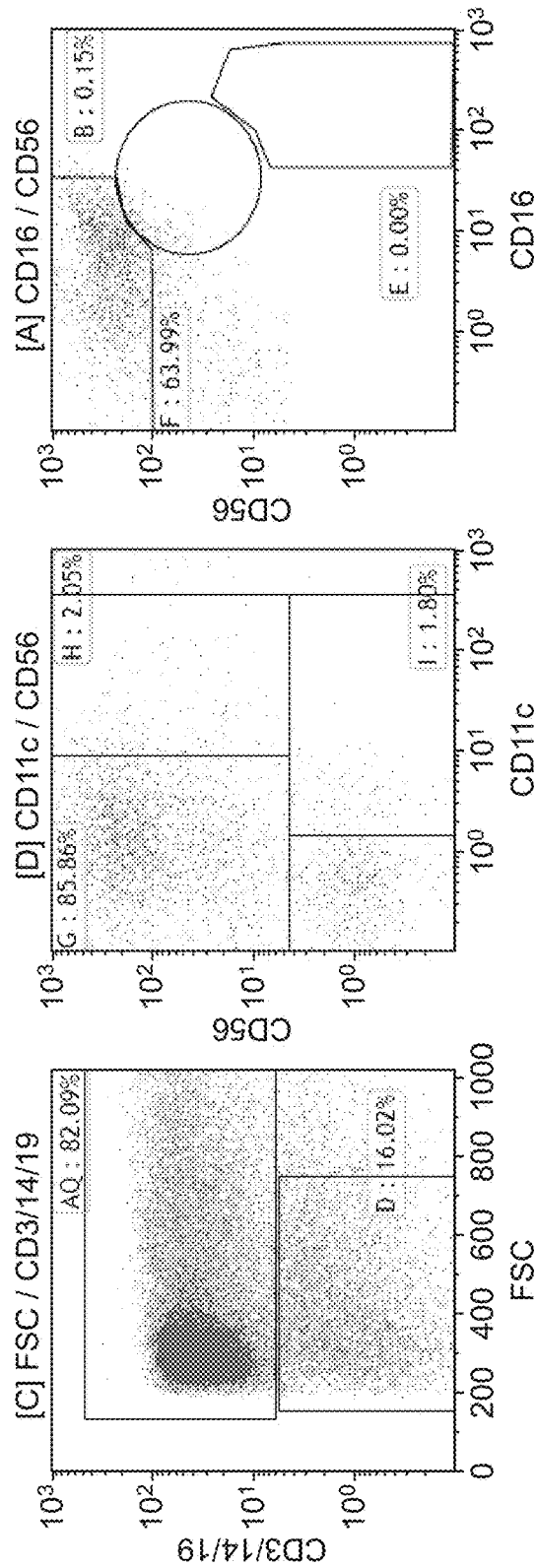

ated natural killer cells having a unique phenotype to satisfy these and other needs. The cells can be used in autologous therapy or in non-autologous therapy.
MODIFIED NATURAL KILLER CELLS, COMPOSITIONS AND USES THEREOF

CROSS-REFERENCE TO RELATED APPLICATIONS

This application claims the benefit of U.S. Application No. 61/923,354, filed on 3 Jan. 2014, the entire disclosure of which is incorporated herein by reference.

FIELD

The invention relates to modified natural killer (NK) cells and pharmaceutical compositions comprising the same. Methods are provided for identifying depleted natural killer (NK) cells and culturing of modified NK cells.

BACKGROUND

Immune surveillance plays a critical role against cancer and represents a very attractive therapeutic approach, especially in light of the many shortcomings of conventional surgery, radiation and chemotherapies in the management of cancer.

The human body's first line of defense against cancer is the natural killer (NK) cell, with the phenotype $CD3^-$ $CD14^-$ $CD19^-$ $CD56^+$ $CD16^+$ $NGK2D^+$ $CD11c^+$ $HLA-DR^-$ $CD86^-$ $CD83^-$. NK cells are cytotoxic lymphocytes that actively scan the body for abnormal cells, destroying them before they can develop into actual cancer cells. As NK cells patrol the body, they interact with many types of cells using their array of activating and inhibiting surface receptors. Most cancer cells engage the NK cell's activating receptors, which triggers its natural kill response.

These findings support a rationale for develop a NK based therapy against cancer cells and culture methods to generate greater number of therapeutically competent NK cells for clinical applications, as there is still an unmet need for effective treatment and/or prevention for cancer. The present invention provides modified natural killer cells having a unique phenotype to satisfy these and other needs. The cells can be used in autologous therapy or in non-autologous therapy.

SUMMARY OF THE INVENTION

In one embodiment, the present invention provides a modified NK cell comprising a $CD3^-/CD56^+$ NK cell phenotype; and one or more dendritic cell surface antigens selected from HLA-DR, CD83 and CD86.

Some embodiments provide pharmaceutical compositions comprising a modified NK cell described herein and a pharmaceutically acceptable carrier or excipient.

Some embodiments provide methods for inhibiting cancer cells, comprising the administering one or more modified NK cells as described herein in a subject in need thereof.

Other embodiments provide methods of inhibiting cancer calls, comprising administering an effective amount of the modified NK cell of claim 1 to a subject in need thereof, wherein the cancer cells are inhibited.

A fourth embodiment of the present invention provides methods of identifying depleted NK cells from a sample, comprising depleting one or more of the following cell surface antigens from a mononuclear cell in said sample: CD14, CD19 or CD25, wherein said depleted NK cell is substantially free of one or more of the cell surface antigens selected from CD14, CD19 and CD25.

A fifth embodiment of the invention provides compositions comprising a T helper 1 cytokine; and a T cell growth factor.

A sixth embodiment of the present invention provides methods of culturing a modified NK cell, comprising contacting a depleted NK cell with a composition comprising (a) a T helper 1 cytokine; and (b) a T-cell growth factor, wherein the depleted NK cell is substantially free of one or more of the cell surface antigens selected from CD14, CD19 and CD25.

In yet another embodiment, the invention provides methods of culturing modified NK cells, comprising (a) contacting the depleted NK cell with a first composition comprising IFN-γ and IL-15; and (b) contacting the depleted NK cell of step (a) with a second composition comprising IL-15, IL-12 and IFN-γ, wherein the depleted NK cell is substantially free of one or more of the cell surface antigens selected from CD14, CD19 and CD25.

The identification and culturing methods described herein allow for isolation of a greater number of modified NK cells from a fixed amount of a sample (for example, 10 ml of blood).

BRIEF DESCRIPTION OF THE DRAWINGS

Illustrative embodiments of the present invention are described in detail below with reference to the following Figures:

FIG. 2A shows the flow cytometry analysis of $CD14^+$, $CD19^+$ and $CD25^+$ cells using forward scatter (FSC) and side scatter (SCC) measurement systems before cell depletion and FIG. 2B contains the flow cytometry analysis of $CD14^+$, $CD19^+$ and $CD25^+$ cells after cell depletion.

FIGS. 3A-3R are an assembly of flow cytometry images of conventional NK cells, NK cells in U.S. application Ser. No. 13/918,529 and modified NK cells of the present invention. FIGS. 3A-3C and FIGS. 3J-3L illustrate the flow cytometry analysis of the conventional NK cells for CD56, CD11c, CD16, HKG2D, HLA-DR, CD86 and CD83. FIGS. 3G-3I and FIGS. 3P-3R illustrate the flow cytometry analysis of the modified NK cell of the present invention. FIGS. 3D-3F and FIGS. 3M-3O illustrate the flow cytometry analysis of NK cells in U.S. application Ser. No. 13/918,529.

FIG. 4A shows the % of Caspase 6 positive target cells in the absence of modified NK cells and FIG. 4B shows the % of Caspase 6 positive target cells in the presence of modified NK cells of the current invention.

FIGS. 5A-5C are an assembly of flow cytometry analysis of cell division illustrating the effect of modified NK cells on T lymphocyte proliferation. FIG. 5A shows the in vitro proliferation of modified NK cells without allogeneic T lymphocytes, FIG. 5B shows the in vitro proliferation of allogeneic T lymphocytes without modified NK cells and FIG. 5C shows the in vitro proliferation of allogeneic T lymphocytes in the presence of modified NK cells.

DETAILED DESCRIPTION OF THE INVENTION

Figure 1:
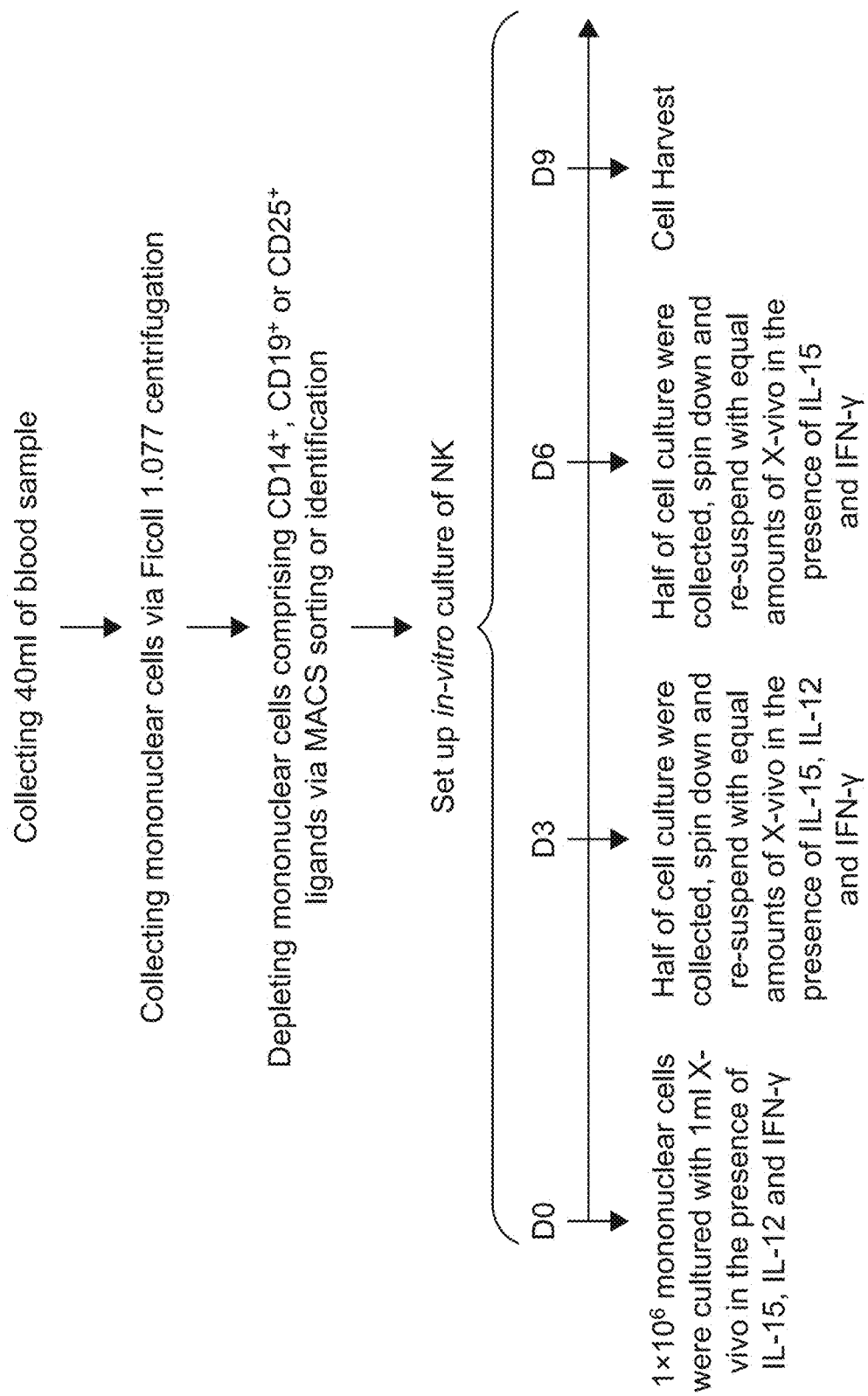
FIG. 1 illustrates schematically the identification steps of depleted NK cells and culturing steps of modified NK cells.

As used herein, the articles "a" and "an" refer to one or more than one (i.e., at least one) of the grammatical object of the article. By way of example, "a modified NK cell" means one modified NK cell or more than one modified NK cell.

An "effective amount," as used herein, refers to a dose of the modified NK cells or pharmaceutical composition that is sufficient to reduce the symptoms and signs of cancer, which include, but are not limited to, weight loss, pain or tumor mass which is detectable, either clinically as a palpable mass or radiologically through various imaging means.

The term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The expression level or surface density of a cell surface antigen, such as CD83, CD86, HLA-DR, on the surface of NK cells are "+" as long as the expression is positive relative to a negative control population, expressed as "−".

All numbers herein may be understood as modified by "about."

Modified NK Cell

Naturally occurring or conventional NK cells have $CD3^-/CD56^+$ phenotype. In one embodiment, the naturally occurring or conventional NK cells have $CD3^-$ $CD14^-$ $CD19^-$ $CD56^+$ $CD16^+$ $NKG2D^+$ $CD11c^+$ phenotype, as illustrated in Table 1.

In one embodiment, the present invention provides a modified NK cell comprising a $CD3^-/CD56^+$ NK cell phenotype; and one or more dendritic cell surface antigens selected from HLA-DR, CD83 and CD86, as illustrated in Table 1. The modified NK cell of the present invention is non-naturally occurring. The modified NK cells comprise one or more of the fully activated dendritic cell surface antigens (for example, HLA-DR, CD83 and CD86) and possess both NK cell function and dendritic cell function and an enhanced anti-cancer activity.

In one embodiment, the modified NK cell is substantially free of CD11c (having a phenotype of $CD3^-$ $CD56^+$ $CD11^-$). In another embodiment, the modified NK cell comprises one or more of the NK cell phenotype selected from $CD14^-$, $CD19^-$, $CD16^+$ and $NKG2D^+$ (having a phenotype of, for example, $CD3^-$ $CD14^-$ $CD19^-$ $CD56^+$ $CD16^+$ $NKG2D^+$). In yet another embodiment, the modified NK cell is substantially free of CD14 and/or CD19.

In one exemplary embodiment, the present invention provides a modified NK cell comprising a $CD3^-/CD56^+$ phenotype NK cell, wherein said $CD3^-/CD56^+$ NK cell further comprises a CD83 cell surface antigen (having a phenotype of $CD3^-$ $CD56^+$ $CD83^+$). In another exemplary embodiment, the present invention provides a modified NK cell comprising a $CD3^-/CD56^+$ phenotype NK cell, wherein $CD3^-/CD56^+$ said NK cell further comprises a CD86 cell surface antigen (having a phenotype of $CD3^-$ $CD56^+$ $CD86^+$). In yet another exemplary embodiment, the present invention provides a modified NK cell comprising a $CD3^-/CD56^+$ phenotype NK cell, wherein said $CD3^-/CD56^+$ NK cell further comprises a HLA-DR cell surface antigen (having a phenotype of $CD3^-$ $CD56^+$ $HLA-DR^+$).

A fourth exemplary embodiment provides a modified NK cell comprising a $CD3^-/CD56^+$ phenotype NK cell, wherein said $CD3^-/CD56^+$ NK cell further comprises a CD83 cell surface antigen and a CD86 cell surface antigen (having a phenotype of $CD3^-$ $CD56^+$ $CD86^+$ $CD83^+$). A fifth exemplary embodiment provides a modified NK cell comprising a $CD3^-/CD56^+$ phenotype NK cell, wherein said $CD3^-/CD56^+$ NK cell further comprises a CD86 cell surface antigen and a HLA-DR cell surface antigen (having a phenotype of $CD3^-$ $CD56^+$ $CD86^+$ $HLA-DR^+$). A sixth exemplary embodiment provides a modified NK cell comprising a $CD3^-/CD56^+$ phenotype NK cell, wherein said $CD3^-/CD56^+$ NK cell further comprises a HLA-DR cell surface antigen and a CD83 cell surface antigen (having a phenotype of $CD3^-$ $CD56^+$ $HLA-DR^+$ $CD83^+$).

In some exemplary embodiments, the present invention provides a modified NK cell comprising a $CD3^-/CD56^+$ phenotype NK cell, wherein said $CD3^-/CD56^+$ NK cell further comprises a HLA-DR cell surface antigen, a CD83 cell surface antigen and a CD86 cell surface antigen (having a phenotype of $CD3^-$ $CD56^+$ $CD86^+$ $HLA-DR^+$ $CD83^+$).

In one embodiment, the expression level or surface density of the cell surface antigen is quantified by exposing the modified NK cells to a fluorescent dye-tagged specific anti-human monoclonal antibody (e.g., CD86-PE (Beckman Coulter; Cat. No: IM2729U) or Anti-human CD83-PE-Cy5 (BioLegend; Cat. No: 305310)), followed by sorting of the modified NK cells using flow cytometry (e.g. Gallios, commercially available from Beckman Coulter, Inc., USA).

The modified NK cells can be from a single individual, i.e., autologous, or pooled from multiple individuals (non-autologous allogeneic).

TABLE 1

Phenotypes of conventional NK cells and modified NK cells

|  | CD3 | CD14 | CD19 | CD56 | CD16 | NKG2D | CD11c | HLA-DR | CD86 | CD83 |
|---|---|---|---|---|---|---|---|---|---|---|
| Conventiona NK | − | − | − | + | + | + | + | − | − | − |
| Modified NK | − | − | − | + | + | + | − | + | + | + |

Pharmaceutical Composition

In one embodiment, the present invention provides pharmaceutical compositions comprising a modified NK cell described herein, and a pharmaceutically acceptable carrier or excipient.

The invention also provides methods of inhibiting cancer cells by administering to a subject in need thereof the present modified NK cells or the present pharmaceutical composition in an amount effective to inhibit cancer cells. Without being bound by any particular theory, it is believed that the modified NK cells inhibit cancer cells by one or more of the NK cell/dendritic cell functions: enhancing cytotoxicity, stimulating cancer-specific T lymphocyte proliferation or IFNγ secretion.

Routes of administration of the present pharmaceutical compositions or modified NK cells include, but are not limited to, intravenous, intramuscular, subcutaneous, oral, topical, subcutaneous, intradermal, transdermal, subdermal, parenteral, rectal, spinal, or epidermal administration. In one embodiment, the modified NK cells are administered by intravenous injection or infusion.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or other particulate carriers used for sustained delivery. For example, the pharmaceutical composition can be in the form of an oil emulsion, water-in-oil emulsion, water-in-oil-in-water emulsion, site-specific emulsion, long-residence emulsion, sticky emulsion, micro emulsion, nano emulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the pharmaceutical composition.

The present modified NK cells are formulated into pharmaceutical compositions for delivery to a mammalian subject. The pharmaceutical composition is administered alone, and/or mixed with a pharmaceutically acceptable vehicle, excipient or carrier. Suitable vehicles are, for example, saline, dextrose, glycerol, or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextran, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers.

Actual methods of preparing such dosage forms are known, or will be apparent, to those skilled in the art. See, e.g., Remington's Pharmaceutical Sciences, Mack Publishing Company, Easton, Pa., 21st edition.

The modified NK cells or the present pharmaceutical compositions can be administered in a single dose treatment or in multiple dose treatments on a schedule and over a time period appropriate to the age, weight and condition of the subject, the particular composition used, and the route of administration, whether the modified NK cells or the present pharmaceutical composition is used for prophylactic or curative purposes, etc. For example, in one embodiment, the modified NK cells or pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of the modified NK cells or the pharmaceutical composition according to the invention, e.g., the period of time over which the modified NK cell or pharmaceutical composition is administered, can vary, depending on any of a variety of factors, e.g., subject response, etc. For example, the modified NK cells or pharmaceutical composition can be administered over a period of time ranging from about one or more seconds to one or more minutes, one or more hours to one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

It is advantageous to formulate parenteral pharmaceutical compositions or modified NK cells in dosage unit form for ease of administration and uniformity of dosage. Dosage unit form as used herein refers to physically discrete units suited as unitary dosages for the subject to be treated; each unit containing a predetermined quantity of modified NK cells calculated to produce the desired therapeutic effect in association with the required pharmaceutical carrier.

The data obtained from the cell culture assays and animal studies can be used in formulating a range of dosage for use in humans. In one embodiment, the dosage of such NK cells lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the modified NK cells which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

The pharmaceutical composition is formulated to contain an effective amount of the present modified NK cells, wherein the amount depends on the animal to be treated and the condition to be treated. The specific dose level for any particular subject depends upon a variety of factors including the activity of the specific modified NK cells, the age, body weight, general health, sex, diet, time of administration, route of administration, and rate of excretion, drug combination and the severity of the particular disease undergoing therapy. An exemplary, non-limiting range for a therapeutically or prophylactically effective amount of the modified NK cells of the present invention is at least about $1 \times 10^3$ cells per dose to about $1 \times 10^9$ per dose. Other dosages are also possible, including, but not limited to, $1 \times 10^4$, $1 \times 10^5$, $1 \times 10^6$, $1 \times 10^7$, $1 \times 10^8$ or $1 \times 10^9$.

The modified NK cells or the pharmaceutical composition can be administered alone or in combination with another therapeutic agent, e.g., chemotherapy, radiotherapy or targeted therapy or cancer vaccine.

Methods of Identifying and Culturing the Modified NK Cells

In one embodiment, the methods of identifying depleted NK cells and culturing the modified NK cells are illustrated in FIG. 1. Modified NK cell culture uses depleted NK cells (purified $CD14^-CD19^-CD25^-$ mononuclear cells) as the initial cell population for the expansion culture.

In one embodiment, as shown in FIG. 1, the identification/depletion steps to obtain a highly purified fraction of $CD14^-CD19^-CD25^-$ mononuclear cells (depleted NK cells) are as follows:
  (a) Collecting a sample from a subject. The sample includes, but is not limited to, any body fluid containing one or more mononuclear cells, such as peripheral blood, cord blood or bone marrow sample.
  (b) Separating the mononuclear cells within the sample in step (a) from other types of blood cells via centrifugation (Ficoll-Paque™ PREMIUM, GE Healthcare USA). Other methods of separating mononuclear cells are known, or will be apparent, to those skilled in the art.
  (c) Depleting one or more mononuclear cells comprising CD25 cell surface antigen (for example, mononuclear cells phenotypes $CD25^+ CD3^-$ and $CD25^+ CD3^+$), CD 14 cell surface antigen or CD 19 cell surface antigen from the other mononuclear cells in step (b), for example, by MACS sorting (Mitenyi Biotec, Germany).
  (d) Collecting the $CD14^-CD19^-CD25^-$ mononuclear cells (or depleted NK cells) in step (c) for culture.

One embodiment of the invention provides methods for identifying a depleted NK cell from a sample, comprising depleting one or more of the following cell surface antigens from a mononuclear cell in said sample: CD14, CD19 or CD25, wherein said depleted NK cell is substantially free of one or more of the cell surface antigens selected from CD14, CD19 and CD25.

In one embodiment, the mononuclear cells comprising CD25 in Step (b) are depleted in the sample. In another embodiment, the mononuclear cells comprising CD14 in Step (b) are depleted in the sample. In yet another embodiment, the mononuclear cells comprising CD19 in Step (b) are depleted in the sample. In yet another embodiment, one or more mononuclear cells comprising CD14 and one or more mononuclear cells comprising CD25 in Step (b) are depleted in the sample. In yet another embodiment, one or more mononuclear cells comprising CD14 and one or more mononuclear cells comprising CD19 in Step (b) are depleted in the sample. In yet another embodiment, one or more mononuclear cells comprising CD19 and one or more mononuclear cells comprising CD25 in Step (b) are depleted in the sample. In yet another embodiment, one or more mononuclear cells comprising CD19, one or more mononuclear cells comprising CD25 and one or more mononuclear cells comprising CD14 in Step (b) are depleted in the sample.

In one embodiment, substantially all of the mononuclear cells comprising CD25 are depleted in the sample. In another embodiment, substantially all of the mononuclear cells comprising CD14 are depleted in the sample. In yet another embodiment, substantially all of the mononuclear cells comprising CD19 are depleted in said sample.

In one embodiment, as shown in FIG. 1, a highly purified fraction of $CD14^-CD19^-CD25^-$ mononuclear cells (or depleted NK cells) are in contact with a culture composition comprising a T cell growth factor and a T help 1 cytokine.

In another embodiment, the $CD14^-CD19^-CD25^-$ mononuclear cells in step (c) (or depleted NK cells) are mixed with a composition comprising a T cell growth factor, a T help 1 cytokine and IL-12. Non limiting example of T cell growth factor is IL-15. Non limiting examples of T helper 1 cytokine include Interferon gamma (IFNγ). In another embodiment, the composition further comprises a hematopoietic cell medium. Non limiting example of the hematopoietic cell medium includes X-vivo 20 (commercially available from Lonza, Switzerland).

In one embodiment, the culture composition is substantially free of one or more the growth factors selected from: stem cell factor, FTL3 ligand, IL-2, IL-7, IL-21 and nicotinamide. In another embodiment, stem cell factor, FTL3 ligand, IL-2, IL-7, IL-21 or nicotinamide; is present in the culture composition in an amount of ≤2 weight %, ≤1.5 weight %, ≤1 weight %, and ≤0.5 weight %.

In one embodiment, the composition comprising a T cell growth factor and a T help 1 cytokine is used for culture the modified NK cells, in the presence of 5% $CO_2$ at 37° C.

The composition according to some embodiments of the invention enhances the proliferation of the modified NK cells. In one embodiment, the composition enhances the expression of fully activated dendritic cell markers such as HLA-DR, CD83 and CD86 cell surface antigens on the modified NK cells. In another embodiment, the composition substantially reduces the expression of CD11c cell surface antigens on the modified NK cells. Proliferation rate of the modified NK cells was determined by FACS, based on the signal intensity of $CD3^-CD14^-CD19^-CD56^+CD11c^-$ cells. Other assays for cell proliferation are well known in the art, e.g., clonogenic assays, metabolic assays, and direct proliferation assays.

An exemplary non-limiting range for the contact time of the $CD14^-CD19^-CD25^-$ mononuclear cells and the composition is from about 1 minute to about 1 hour, from about 1 hour to about 24 hours, from about 1 day to about 3 days, from about 1 day to about 6 days, from about 1 day to about 9 days, from about 3 days to about 6 days, or at least 1 day. In one embodiment, the contact time is about 3 days. In another embodiment, the contact time is about 6 days.

In one embodiment, the $CD14^-CD19^-CD25^-$ mononuclear cells (or depleted NK cells) are in contact with a first composition comprising an IL-15, an IFNγ and an IL-12; followed by contacting with a second composition comprising an IL-15 and an IFNγ. In another embodiment, the first and second compositions further comprise a hematopoietic cell medium, such as X-vivo 20.

IL-12 is toxic to NK cells. Therefore, the concentration of IL-12 in the composition is critical for culturing and expansion of viable modified NK cells, as a higher concentration of IL-12 lead to a lower harvest of viable modified NK cells (see FIG. 6). In one embodiment, the effective concentration of IL-12 is less than or equal to 15 ng/ml, such as, for example, 14.5, 14, 13.5 ng/ml. In another embodiment, the effective concentration of IL-12 is greater than 0.1 ng/ml, such as, for example, 0.15, 0.2, 0.25 ng/ml. In yet another embodiment, the effective concentration of IL-12 is about 0.1 to about 5 ng/ml, or any value or range of values there between in 0.1 ng/ml increments (e.g., about 0.6 ng/ml, about 4.3 ng/ml, etc.). In yet another embodiment, the effective concentration of IL-12 is equal to about 5 to about 10 ng/ml or any value or range of values there between in 0.1% increments (e.g., about 6.5 ng/ml, about 8.2 ng/ml etc.). In yet another embodiment, the effective concentration of IL-12 is equal to about 10 to about less than 15 ng/ml or any value or range of values there between in 0.1% increments (e.g., about 13.7 ng/ml, about 12.8 ng/ml etc.).

The following examples of specific aspects for carrying out the present invention are offered for illustrative purposes only, and are not intended to limit the scope of the present invention in any way.

EXAMPLES

Example 1: Identification of the Modified NK Cells 40 ml of peripheral blood was collected from a healthy volunteer into vacuum tubes containing K2EDTA. The blood sample was mixed with equal volume of pre-warmed phosphate-buffered saline (PBS) (Biological Industries, Israel). The 40 ml diluted peripheral blood aliquot was placed into a 50 ml centrifuge tube and downloaded 10 ml pre-warmed Ficoll-Paque™ PREMIUM. The centrifuge tube was centrifuged at 2000 rpm, in room temperature for 30 min. The mononuclear cells in the interface layer were collected, washed once in PBS. The cell pellet was re-suspended into a density of $10^6$/100 ml MACS buffer.

To deplete CD14$^+$ cells, CD19$^+$ cells and CD25$^+$ cells, the mononuclear cells were subjected to immunomagnetic bead separation using "QuadroMACS Separator" (Miltenyi Biotec Bergisch, Gladbach, Germany), according to the manufacturer's instructions. Briefly, the mononuclear cells were reacted with biotin-anti-CD14, biotin-anti-CD19, and biotin-anti-CD25, separated with a magnetic separator, and the CD14 negative, CD19 negative and CD25 negative cell fraction was purified from unbound cells by washing. The enriched mononuclear cell fraction was substantially free of CD14$^+$ cells, CD19$^+$ cells and CD25$^+$ cells (the depleted NK cells).

Figure 2B:
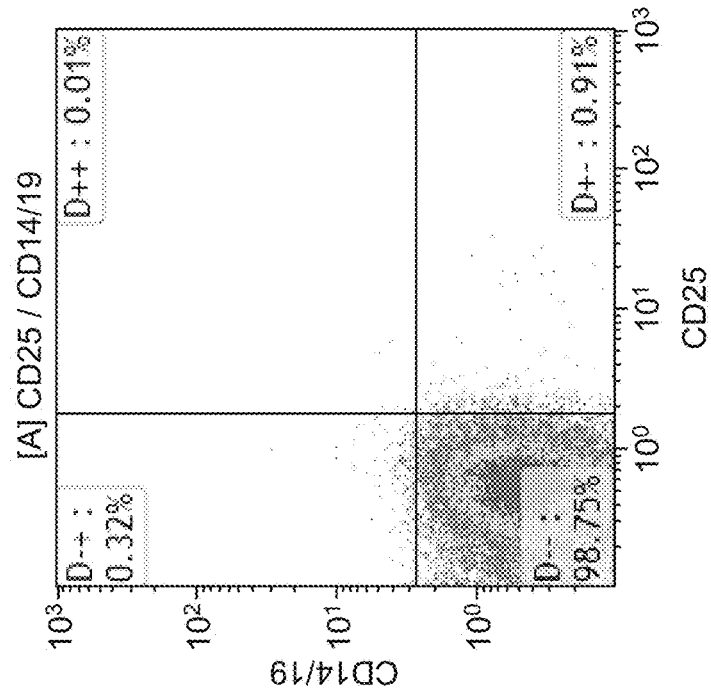
FIGS. 2A and 2B are an assembly of images illustrating the expression level of CD14, CD19 and CD25 cell surface antigens on the NK cells before and after the depletion/identification process.
Figure 2A:
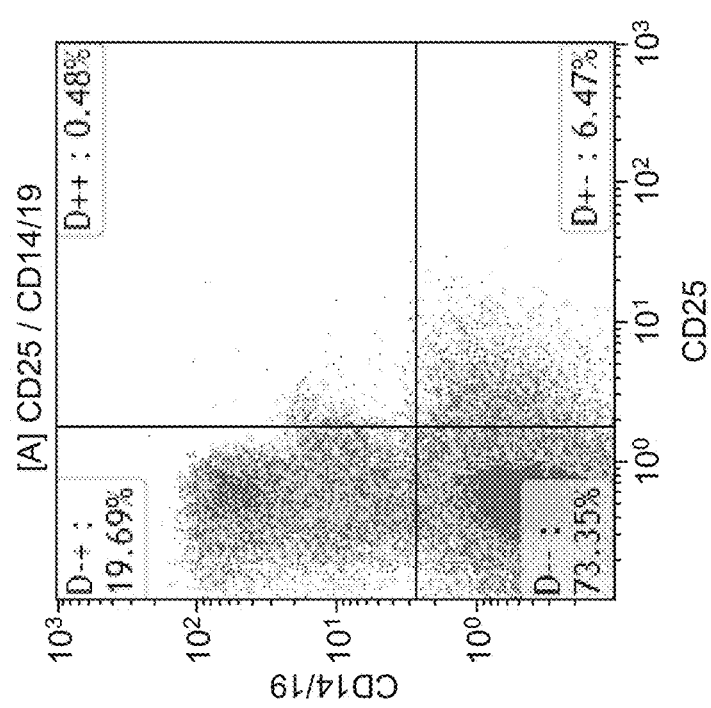

As show in FIG. 2, the signal levels for CD14$^+$ cells, CD19$^+$ cells and CD25$^+$ NK cells were much higher before the depletion (FIG. 2A) than those after the depletion (FIG. 2B).

Example 2: Modified NK Cell Culture

After negative depletion, purified CD14$^-$, CD19$^-$ and CD25$^-$ NK cell (the depleted NK cell) fraction from Example 1 was cultured as follows:

(a) Contacting 1×10$^6$ CD14$^-$/CD19$^-$/CD25$^-$ NK cells (depleted NK cells) with a composition comprising 1 ml of X-vivo 20 medium, 1 ml of IL-15 (concentration: 10 ng/ml), 1 ml of IL-12 (concentration: 4 ng/ml) and 1 ml of IFN-γ (concentration: 20 ng/ml) on day 0.

(b) Harvesting and spinning down half of depleted NK cells in step (a), followed by re-suspending cell pellet with a composition comprising X-vivo 20, 10 ng/ml of IL-15, 4 ng/ml of IL-12 and 20 ng/ml of IFN-γ on day 3. The volume of X-vivo 20 and each of the growth factors used to suspend the cell pellet should be equal to the volume of the cell pellet.

(c) Harvesting and spinning down half of the depleted NK cells in step (b), followed by re-suspending cell pellet with a composition comprising X-vivo 20, 10 ng/ml IL-15 and 20 ng/ml IFN-γ on day 6. The volume of X-vivo 20 and each of the growth factors used to suspend the cells should be equal to the volume of the cell pellet.

(d) Collecting all of the cultured depleted NK cells in step (c) on day 9.

The cultured depleted NK cells in step (d) were assayed for their phenotype using Gallios Flow Cytometer (10 COLORS/3 LASERS, serial number: AU18419, Beckman Coulter, Inc. USA), Kazula software version 1.2 (Beckman Coulter, Inc. USA) and antibodies listed in Table 2.

TABLE 2

Antibodies used for modified NK cells phenotype

1. Anti- human CD3-FITC (Beckman Coulter; Cat. No: IM1281U)
2. Anti- human CD86-PE (Beckman Coulter; Cat. No: IM2729U)
3. Anti- human CD14-PC5.5 (Beckman Coulter; Cat. No: A70204)
4. Anti- human CD16-PE-Cy7 (Beckman Coulter; Cat. No: 6607118)
5. Anti- human CD11c-APC (BioLegend; Cat. No: 301614)
6. Anti- human CD56-APC-Alexa Fluor 700 (Beckman Coulter; Cat. No: B10822)
7. Anti- human CD19-APC-AlexaFluor750 (Beckman Coulter; Cat. No: A78838)
8. Anti- human HLA-DR-Pacific Blue (Beckman Coulter; Cat. No: A74781)
9. Anti- human CD86-Alexa Fluor488 (BioLegend; Cat. No: 305414)
10. Anti- human NKG2D-PE (Beckman Coulter; Cat. No: A08934)
11. Anti- human CD83-PE-Cy5 (BioLegend; Cat. No: 305310)
12. Anti- human CD3-APC-AlexaFluor750 (Beckman Coulter; Cat. No: A66329)
13. Anti- human CD14-APC-AlexaFluor750 (Beckman Coulter; Cat. No: A86052)
14. Anti- human CD25-PE (Beckman Coulter; Cat. No: IM0479U)

In this working example, the expression level or surface density of the cell surface antigen using FACS/flow cytometry analysis are defined in Table 3. The interpretation for the various expression levels in Table 3 is an example of defining the expression level of the cell surface antigen. It should be noted that the flow cytometry signal level intensity varies with the following factors: the flow cytometry, the software and different batches of antibody used.

TABLE 3

| Symbol | Interpretation |
|---|---|
| − | Flow cytometry signal level intensity less than or equal to $10^0$ (i.e., 1) |
| + (Dim) | Flow cytometry signal level intensity between $10^0$ to $10^1$ |
| + | Flow cytometry signal level intensity between $10^1$ to $10^2$ |
| + (hi) | Flow cytometry signal level intensity greater than or equal to $10^2$ |

Results:

As shown in FIGS. 3G-3I and FIGS. 3P-3R, the cultured NK cells have the phenotype of CD3$^-$ CD19$^-$ CD14$^-$ CD56$^+$ CD16$^+$ NKG2D$^+$ CD11c$^-$ CD86$^+$ HLA-DR$^+$ CD83$^+$. FIGS. 3A-3C and 3J-3L illustrate the conventional NK cells have the phenotype of CD3$^-$ CD19$^-$ CD14$^-$ CD56$^+$ CD16$^+$ NKG2D$^+$ CD11c$^+$ CD86$^-$ HLA-DR$^+$ CD83$^-$. FIGS. 3D-3F and 3M-3O illustrate the flow cytometry analysis of the NK cells in U.S. application Ser. No. 13/918,529.

The differences in conventional NK cell phenotype and modified NK cell phenotype are outlined below.

Figures 3A, 3B, 3C:
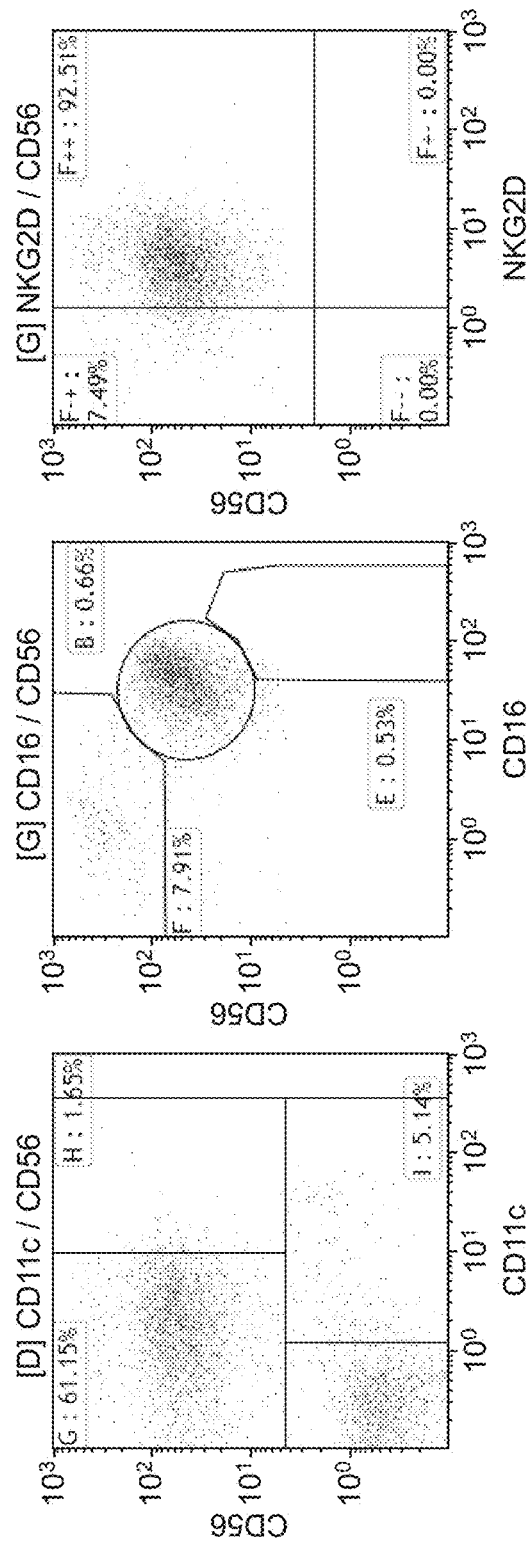
Figures 3G, 3H, 3I:
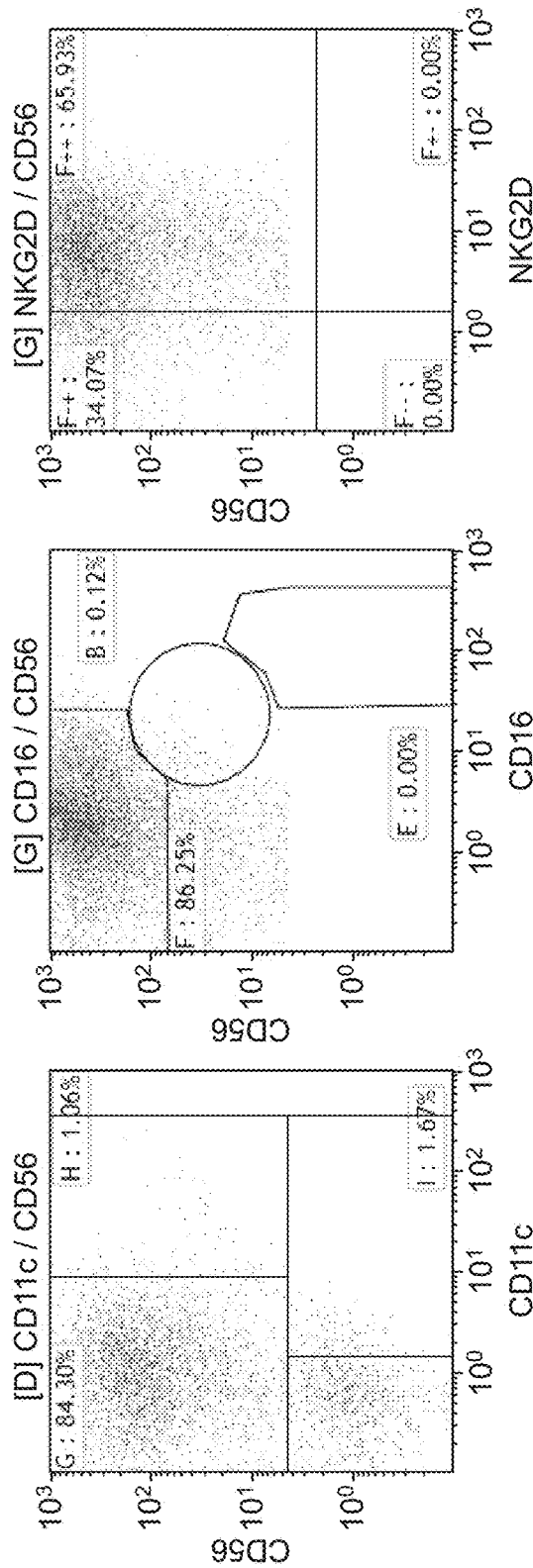

FIG. 3A shows the conventional NK cells having phenotype CD11c$^+$, whereas FIG. 3G shows the modified NK cells having phenotype CD11c$^-$.

Figures 3J, 3K, 3L:
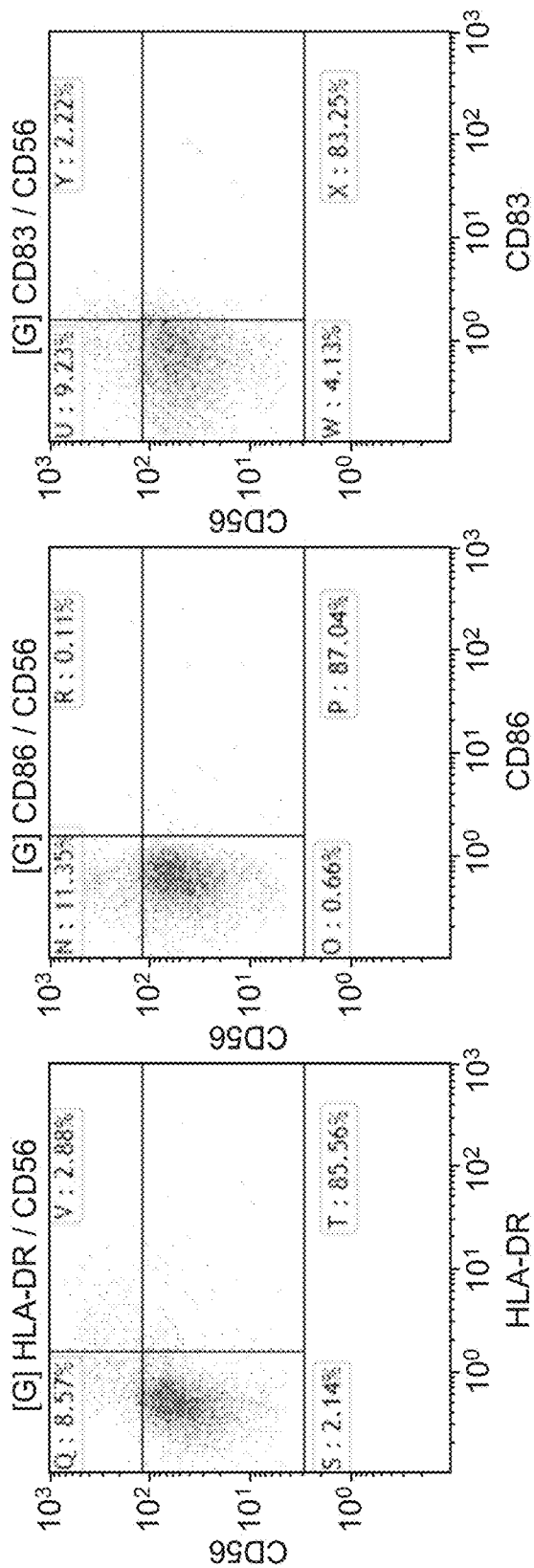
Figures 3M, 3N, 3O:
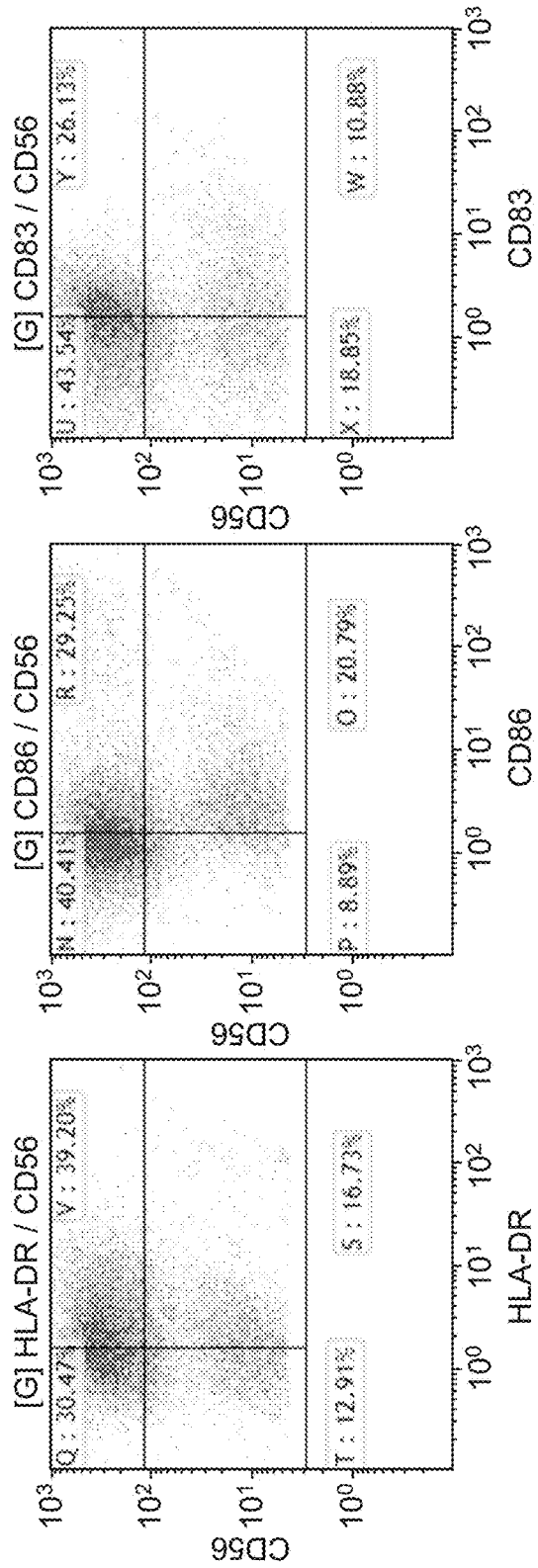
Figures 3P, 3Q, 3R:
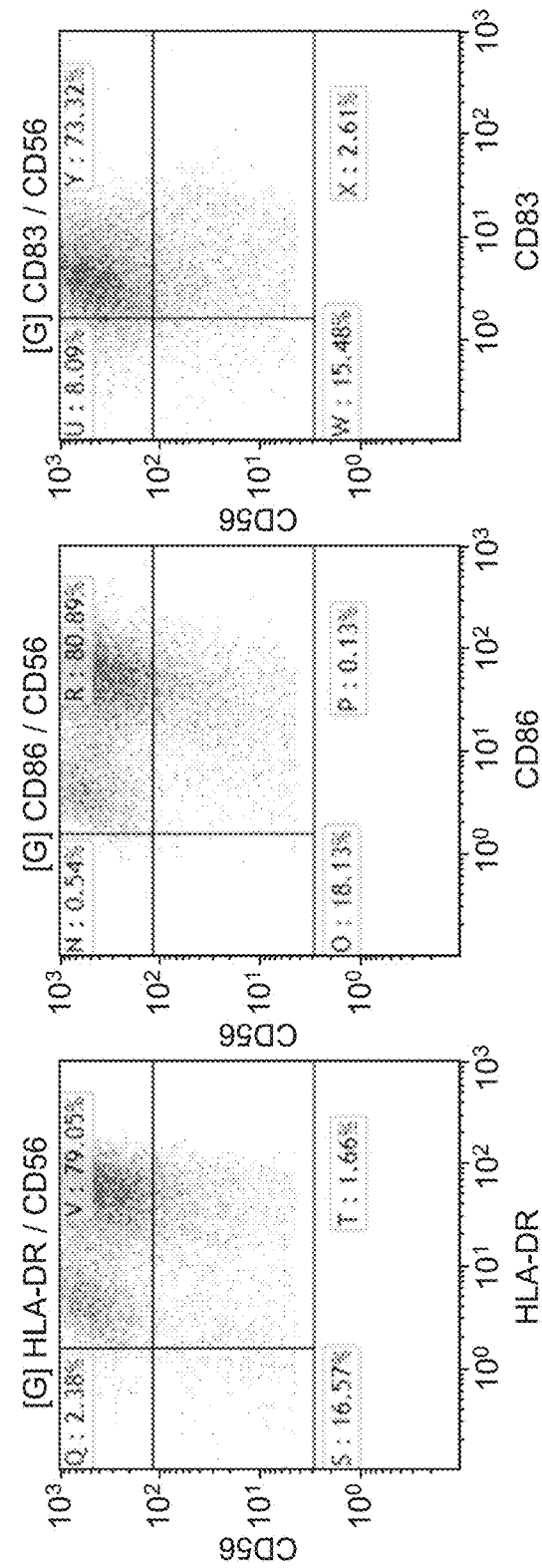

FIG. 3J shows the conventional NK cells having phenotype HLA-DR$^+$ whereas FIG. 3P shows the modified NK cells having phenotype HLA-DR$^+$.

FIG. 3K shows the conventional NK cells having phenotype CD86$^-$ whereas FIG. 3Q shows the modified NK cells having phenotype CD86$^+$.

FIG. 3L shows the conventional NK cells having phenotype CD83$^-$ whereas FIG. 3R shows the modified NK cells having phenotype CD83$^+$.

Example 3: Determination of the Functionality of NK Cells

"Killing" assay: modified NK cells from Example 2 were cultured with APC-labelled K562 leukaemic target cells at 1:1 ratio for 30 minutes. Killing of target cells was determined by FACS as a percentage Capase 6-positive (dead) APC-labeled target cells. A higher % of Capase 6+ cells is indicative of higher level of killing.

Figure 4A:
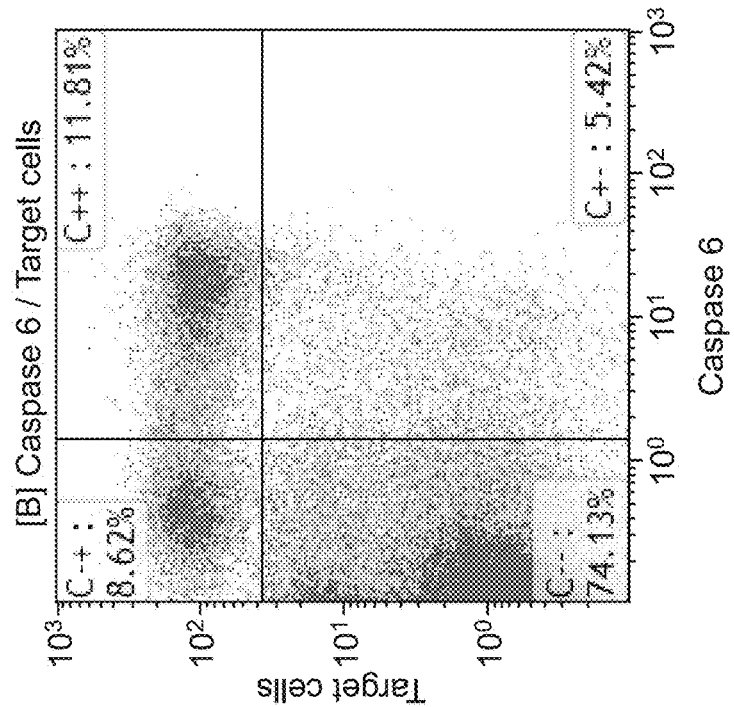
FIGS. 4A and 4B are an assembly of flow cytometry images illustrating the cytotoxicity of the modified NK cells.
Figure 4B:
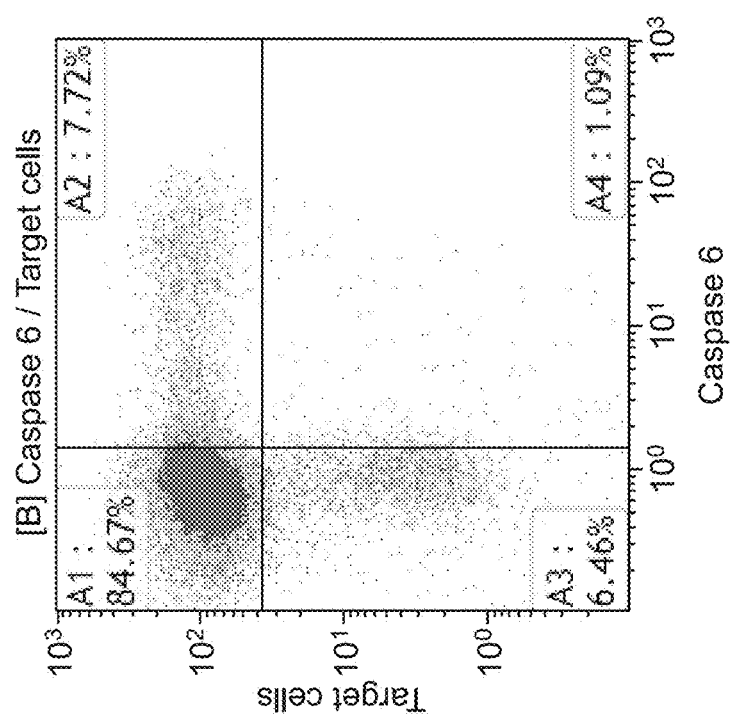

Results:

As shown in FIG. 4A, the % of capase positive target cells (without modified NK cells) was 8.3%, whereas in FIG. 4B, the % of capase positive target cells (with modified NK cells) was 57.8%. This result shows the modified NK cells has a higher cytotoxic effect on the leukaemic target cells.

Assay of T Lymphocyte Proliferation

Modified NK cells from Example 2 were cultured with CFSE-labelled allogeneic T lymphocytes. The proliferation of T lymphocytes led to the secretion of cytokines, such as IFNγ and IL-2. The proliferation of allogeneic T lymphocytes was determined by FACS as the number of CFSE-labelled mononuclear cells.

Results:

The division of a proportion of allogeneic T lymphocytes is higher when cultured with the NK cells of Example 2 (FIG. 5C) and little or no division of allogeneic T lymphocyte when cultured alone, i.e., without the NK cells of Example 2 (FIG. 5B).

Example 4: The Effect of IL-12 Concentration on Modified NK Cell Culture

IL-12 is potentially toxic. An in vitro evaluation of the concentration of IL-12 in a composition was performed using FACS/Flow cytometry.

The following IL-12 concentrations were used in the composition for culturing the NK cells of Example 2: 0 ng/ml IL-12 (no IL-12), 0.18 ng/ml, 0.55 ng/ml, 1.66 ng/ml, 5 ng/ml and 15 ng/ml.

Figure 6:
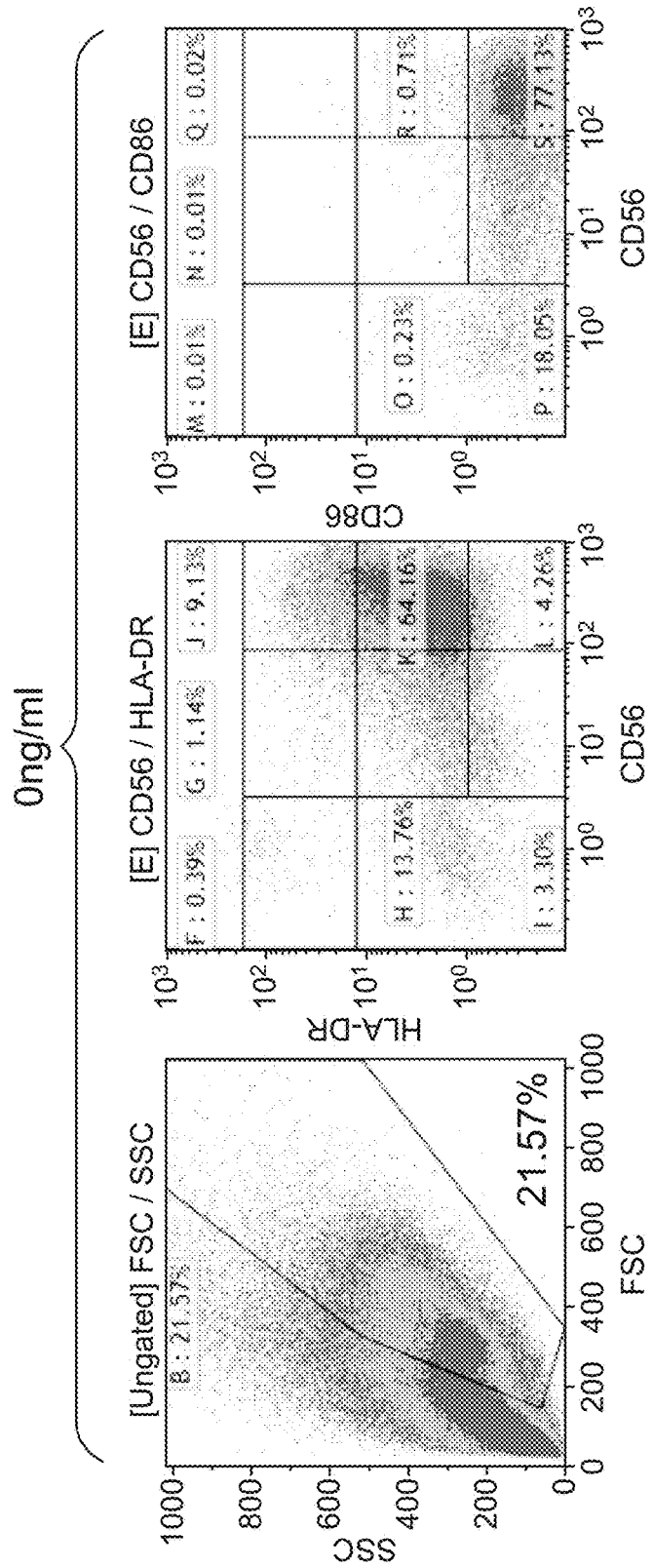
FIG. 6 is an assembly of flow cytometry images showing the effect of various concentrations of IL-12 on modified NK cells.
Figure 6:
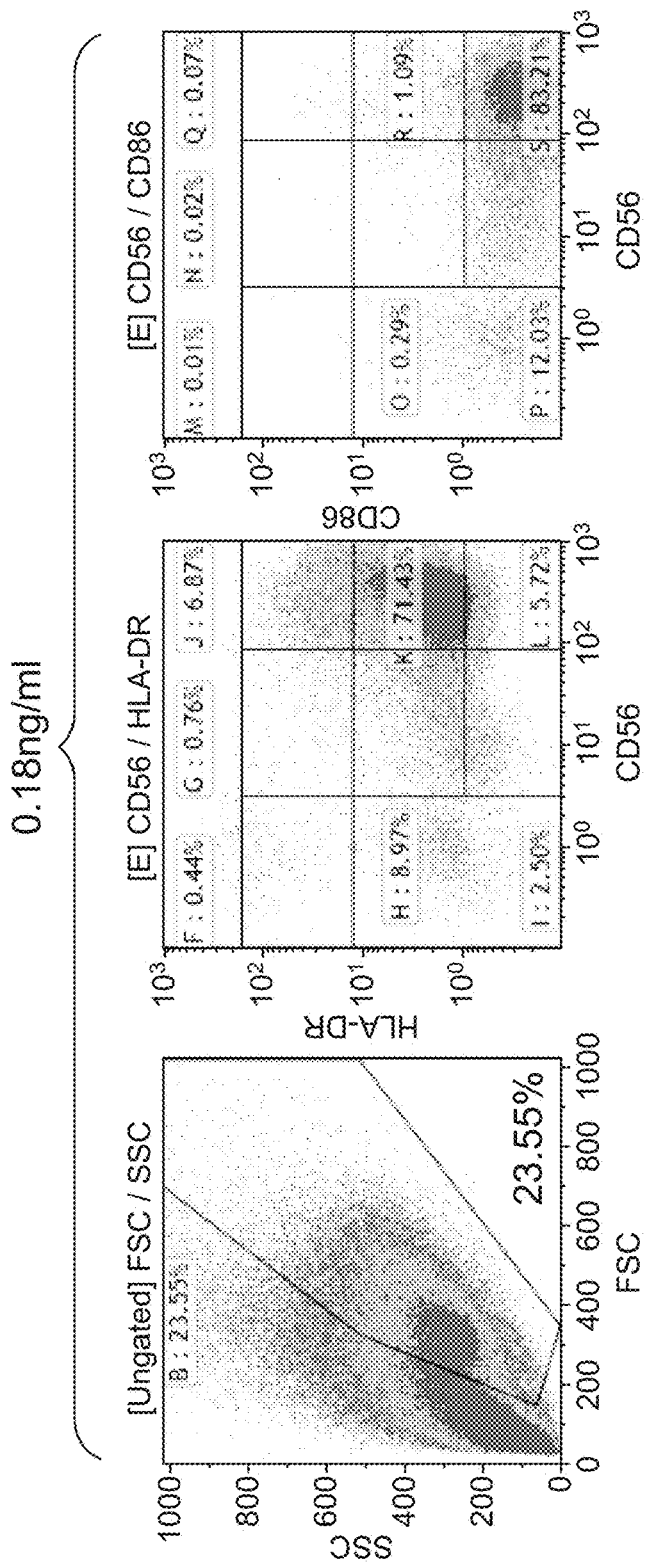
Figure 6:
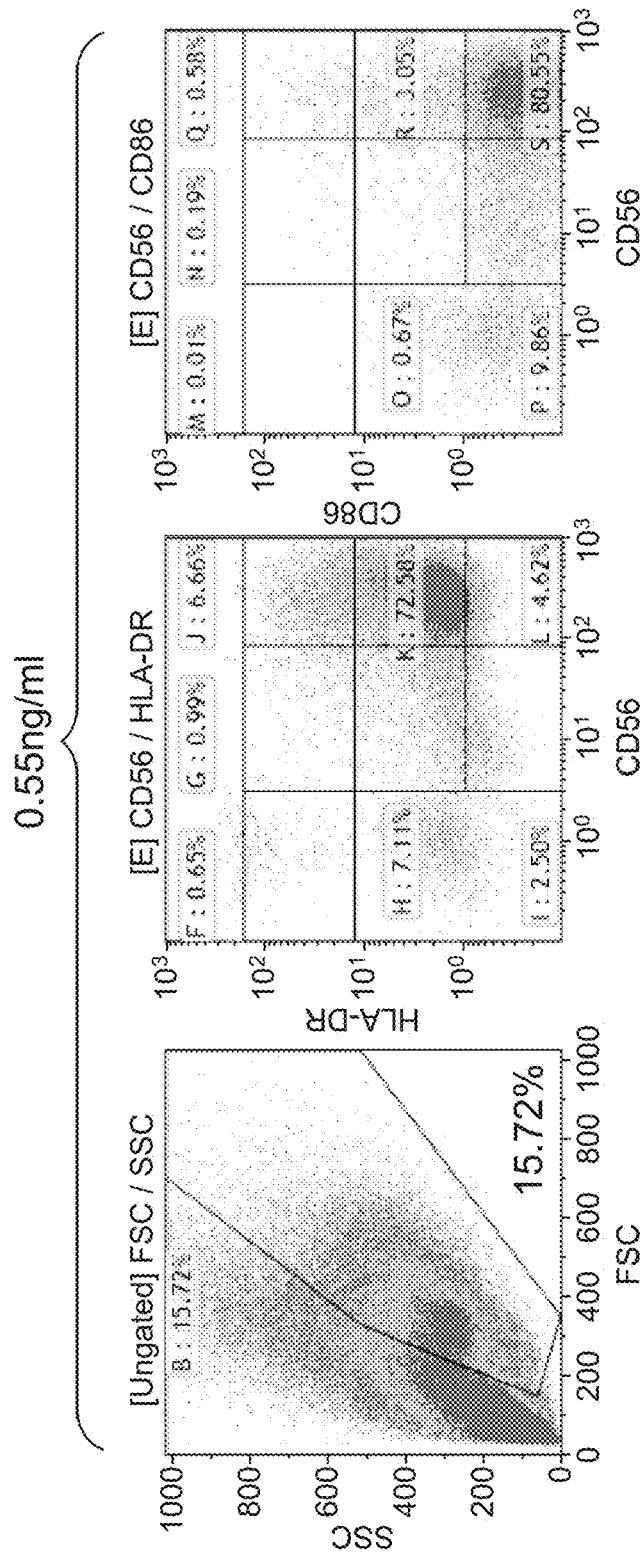
Figure 6:
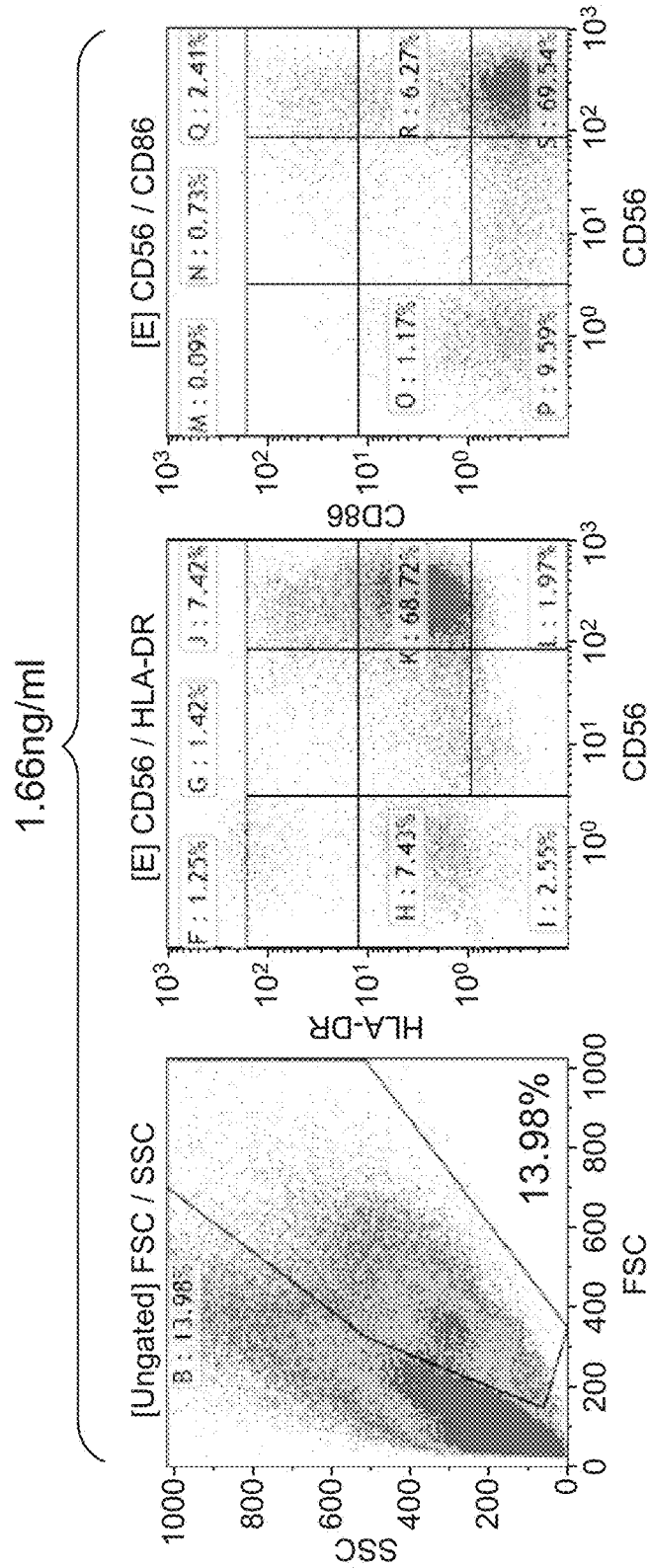
Figure 6:
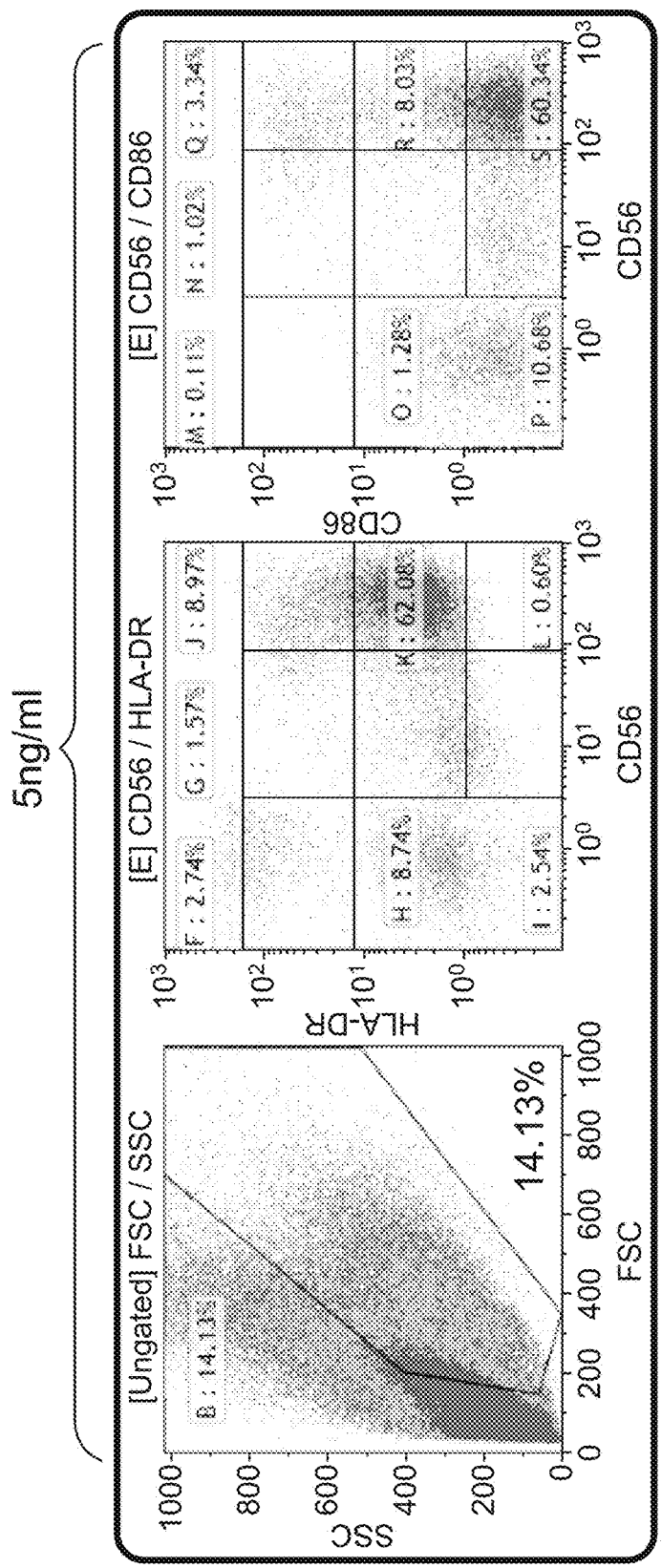
Figure 6:
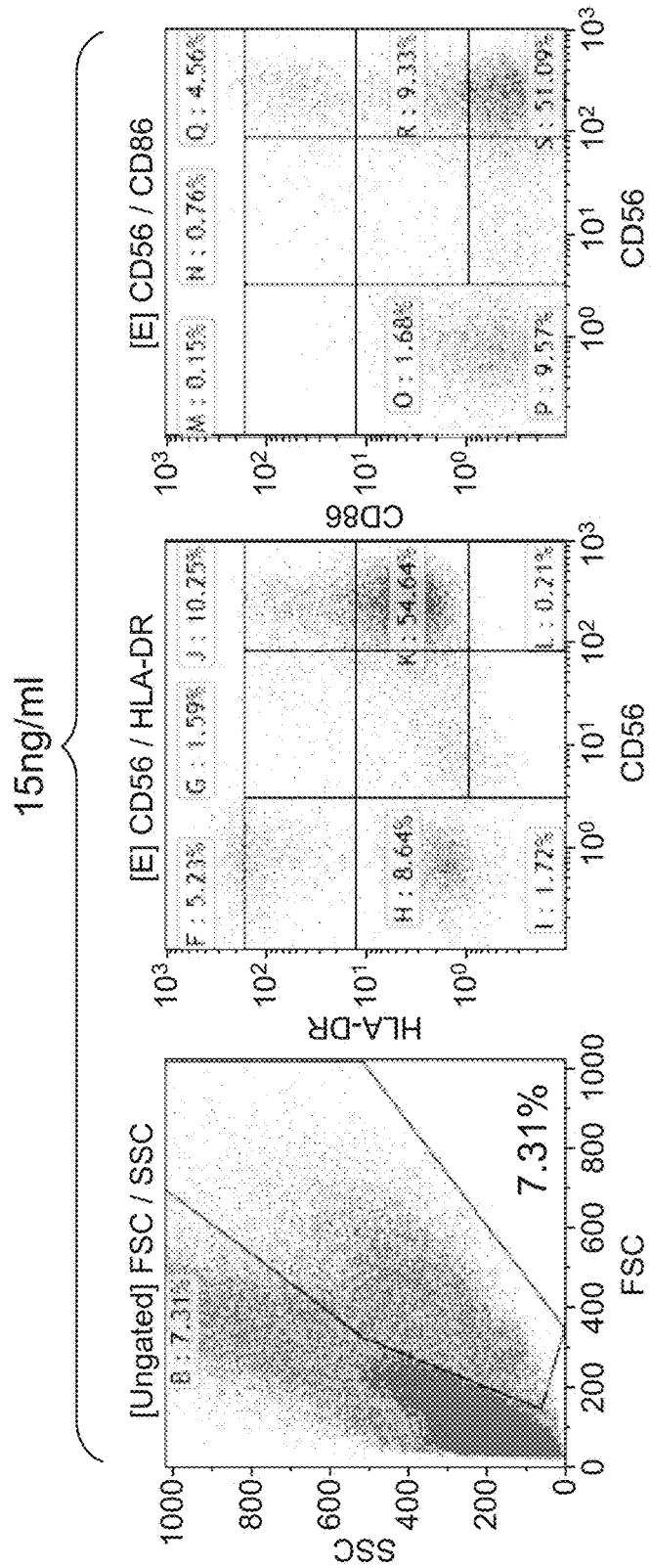

Results:

As shown in FIG. 6, the number of viable NK cells in Example 2 reduces with a higher IL-12 concentration. At an IL-12 concentration of 5 ng/ml, about 14.13% of the cultured NK cells were viable whereas at an IL-12 concentration of 15 ng/ml, only 7.31% of the cultured NK cells were viable.

Example 5: The Effect of IL-2 on Modified NK Cell Culture

An in vitro evaluation of the effect of IL-2 composition and IL-15 composition on modified NK cell culture was performed using FACS/Flow cytometry.

Figures 7A, 7B, 7C:
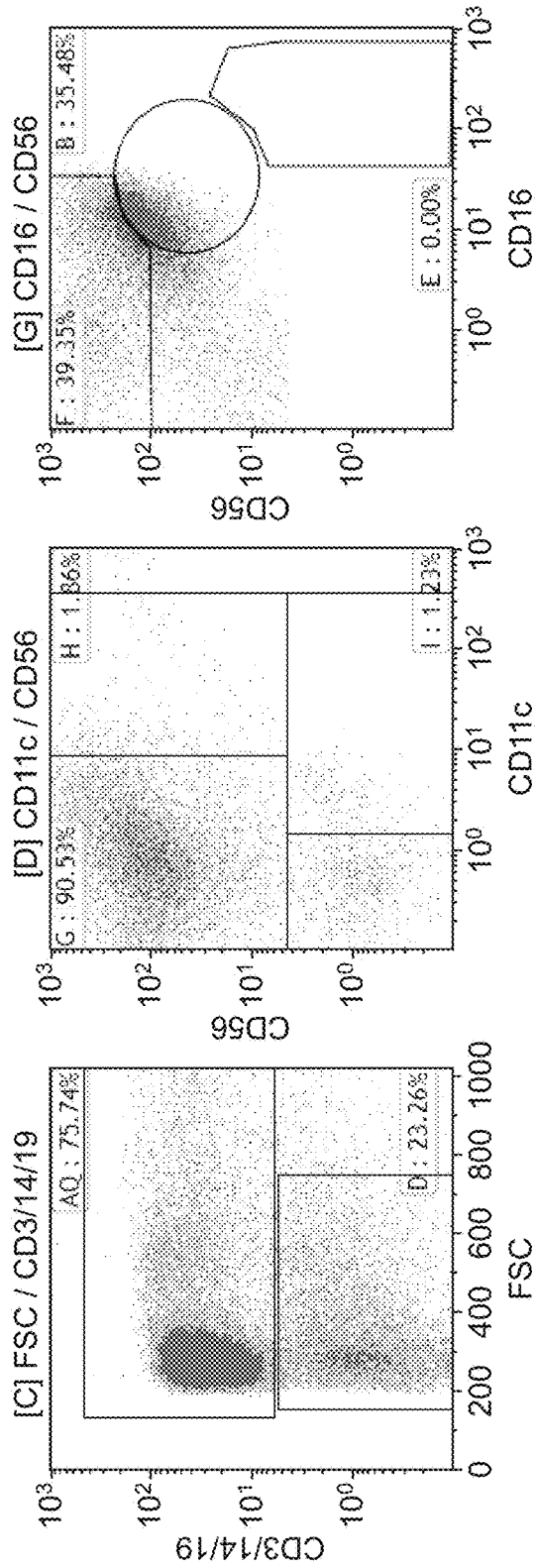
FIGS. 7A-7N are an assembly of flow cytometry images showing the effect of compositions comprising IL-2 (FIGS. 7A-7C, 7G-7I, and 7M) or compositions comprising IL-15 (FIGS. 7D-7F, 7J-7L, and 7N) on the expression of cell surface antigens on the modified NK cells.
Figures 7G, 7H, 7I:
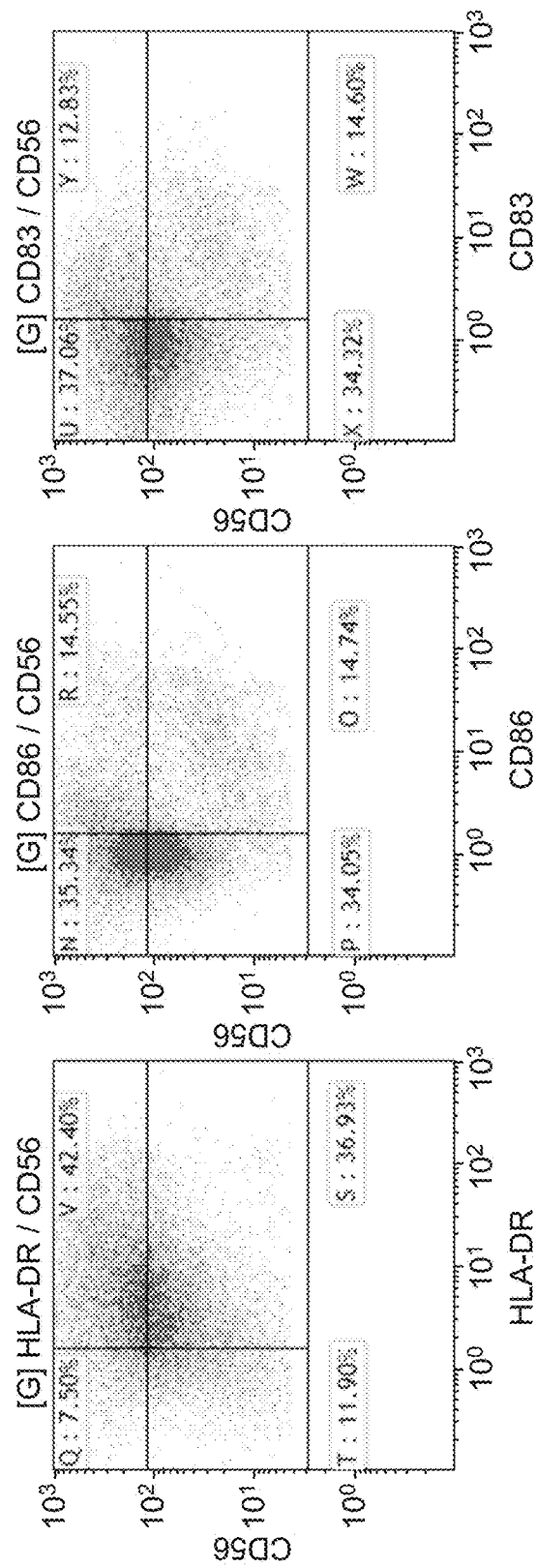
Figures 7J, 7K, 7L:
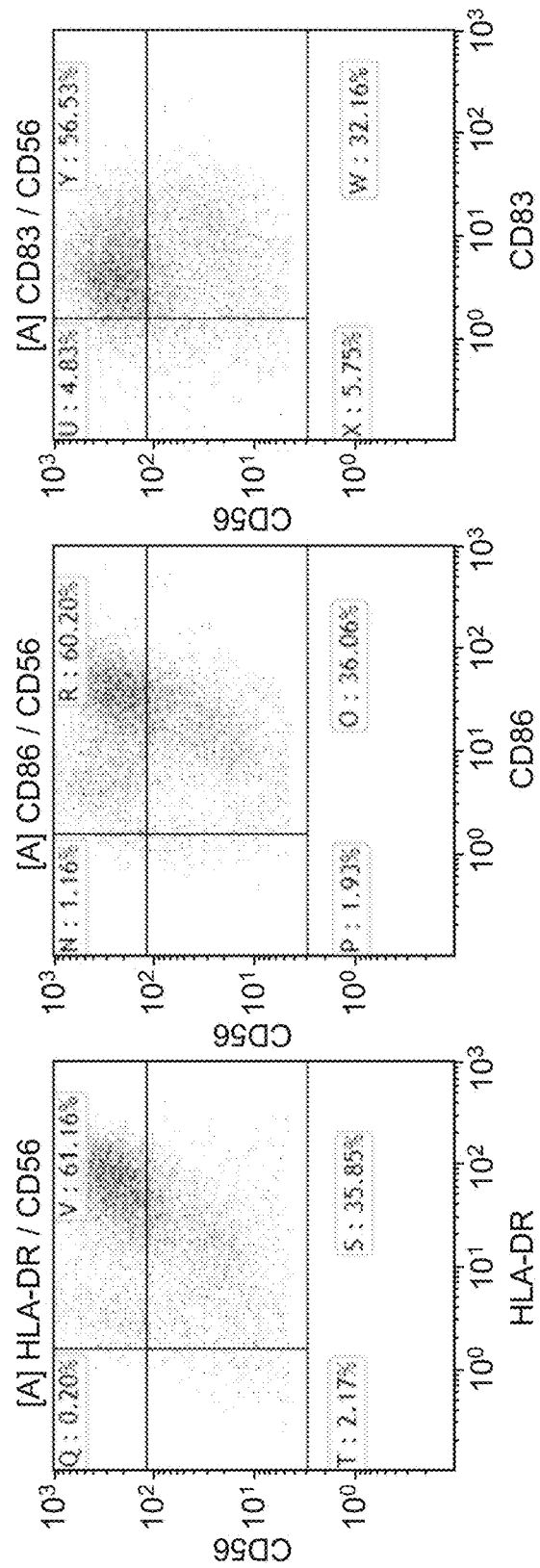
Figures 7M, 7N:
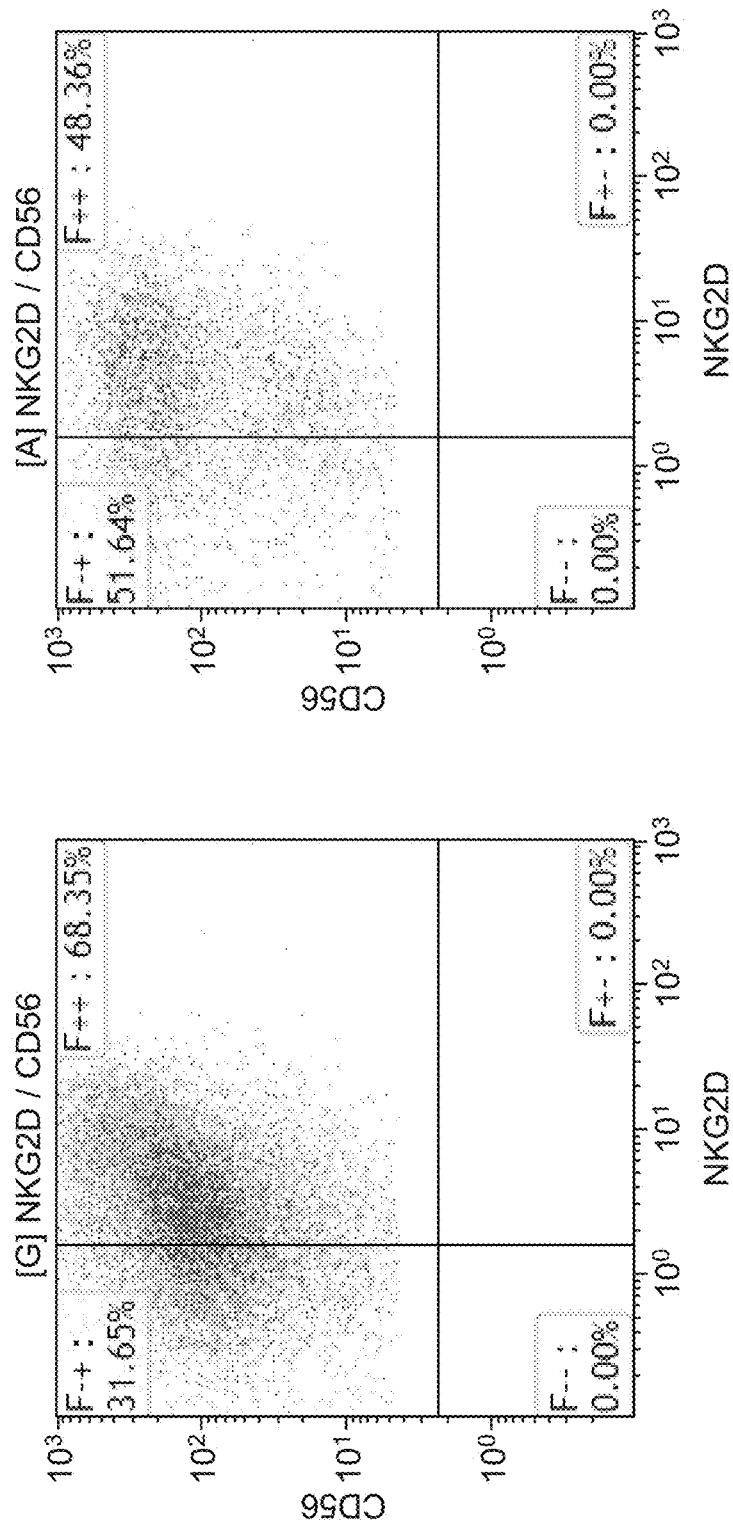

As shown in FIGS. 7H and 7I, CD86 cell surface antigen and CD83 cell surface antigen were not expressed on the NK cells which cultured with a composition comprising IL-2. On the other hand, CD86 cell surface antigen and CD83 cell surface antigen were both expressed on the NK cells which cultured with a composition comprising IL-15, as illustrated in FIGS. 7K and 7L.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method of obtaining a human NK cell possessing both NK cell function and dendritic cell function, comprising the steps of:
   (a) obtaining a human peripheral blood mononuclear cell;
   (b) culturing the human peripheral blood mononuclear cell with IL-15, IL-12, and IFN-γ to obtain a cultured cell population; and
   (c) isolating the human NK cell possessing both NK cell function and dendritic cell function from the cultured cell population with the cell marker $CD3^-CD56^+CD16^+NKG2D^+CD86^+HLA-DR^+CD83^+$.

2. The method of claim 1, wherein a concentration of said IL-12 is about 0.1 ng/ml to less than 15 ng/ml.

3. The method of claim 1, wherein the step (b) further comprises culturing the human NK cell with a hematopoietic cell medium.

4. The method of claim 3, wherein the hematopoietic cell medium is X-vivo 20.

5. The method of claim 1, wherein the step (b) is conducted for one day to 9 days.

6. The method of claim 1, wherein between the step (a) and the step (b), the method further comprises the steps of (z1) depleting $CD14^+$ cells, $CD19^+$ cells, and $CD25^+$ cells to obtain $CD14^-CD19^-CD25^-$ human peripheral blood mononuclear cell and culturing the $CD14^-CD19^-CD25^-$ human peripheral blood mononuclear cell in the step (b).

* * * * *